(12) United States Patent
Rosenfeld

(10) Patent No.: US 8,326,649 B2
(45) Date of Patent: *Dec. 4, 2012

(54) SYSTEM FOR PROVIDING EXPERT CARE TO OUTPATIENTS FROM A REMOTE LOCATION

(75) Inventor: Brian A. Rosenfeld, Baltimore, MD (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 397 days.

This patent is subject to a terminal disclaimer.

(21) Appl. No.: 12/471,510

(22) Filed: May 26, 2009

(65) Prior Publication Data

US 2009/0259495 A1    Oct. 15, 2009

Related U.S. Application Data

(63) Continuation-in-part of application No. 11/072,359, filed on Mar. 4, 2005, and a continuation-in-part of application No. 10/654,668, filed on Sep. 4, 2003, now Pat. No. 7,475,019, and a continuation-in-part of application No. 10/946,548, filed on Sep. 21, 2004, now Pat. No. 7,256,708, and a continuation-in-part of application No. 09/443,072, filed on Nov. 18, 1999, now Pat. No. 6,804,656.

(60) Provisional application No. 60/141,520, filed on Mar. 3, 2009.

(51) Int. Cl.
*G06Q 50/00* (2012.01)

(52) U.S. Cl. ................................. 705/3; 705/2; 600/300
(58) Field of Classification Search .................. 705/2–3; 600/300

See application file for complete search history.

(56) References Cited

U.S. PATENT DOCUMENTS 6,101,478 A * 8/2000 Brown ............................... 705/2
6,329,139 B1 * 12/2001 Nova et al. ...................... 506/30

* cited by examiner

*Primary Examiner* — Sind Phongsvirajati

(57) ABSTRACT

A system for providing expert care to a basic care medical facility (OPCL) from a remote location. The system facilitates real-time, continuous assessment of patients receiving care in an OPCL that is not generally equipped to provide expert medical care on a twenty-four hour basis. Patient monitoring equipment acquires monitored data elements from a patient monitoring station and transmits the monitoring data over a network to a remote command center. The remote command center also receives other patient data to the extent available from the OPCL. Alternatively, the patient monitored data is sent to a remote command center along with patient data at a pre-established time or when requested by remote command center. The delivery of stored monitoring data and patient data may be expedited if an urgent consultation is warranted. A rules engine continuously applies a patient-specific rule or rule set to the data elements selected from the assessment data from each OPCL monitored patient to determine whether intervention is warranted. Patient-specific rules may be created that are consistent with the capabilities of the OPCL.

56 Claims, 10 Drawing Sheets

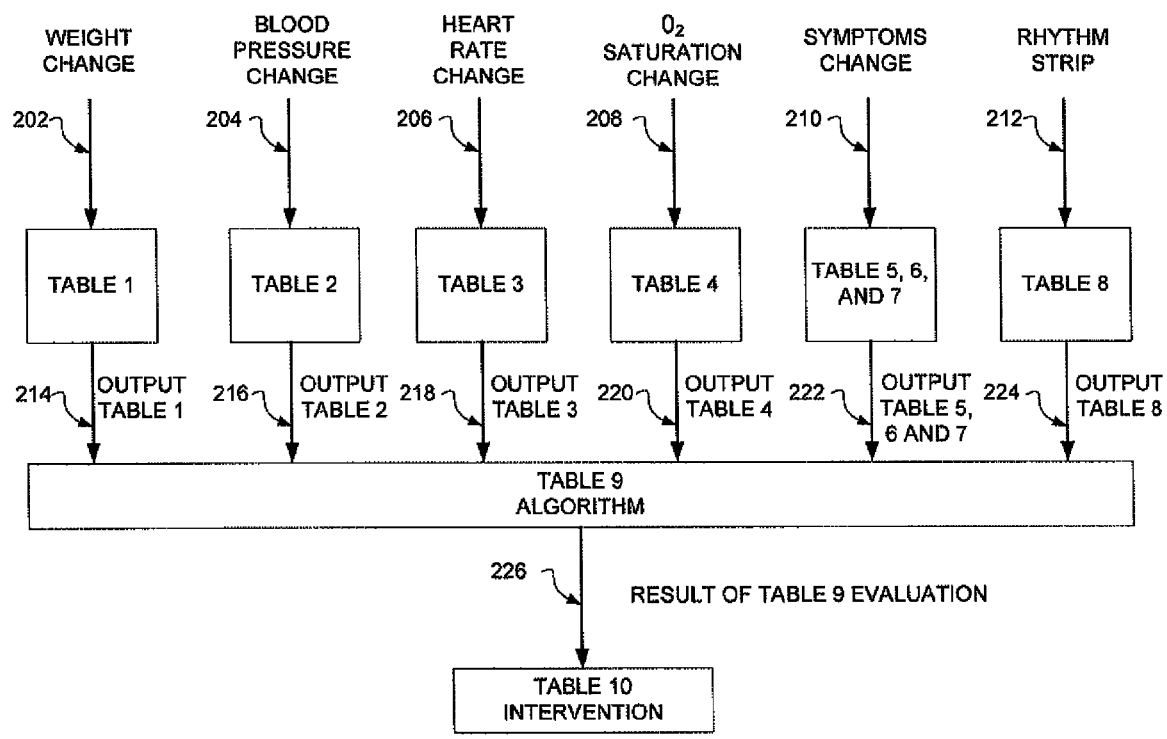

SYSTEM FOR PROVIDING EXPERT CARE TO OUTPATIENTS FROM A REMOTE LOCATION

RELATIONSHIP TO OTHER APPLICATIONS

This application is a continuation-in-part of application Ser. No. 11/072,359 filed Mar. 4, 2005, which is a continuation-in-part of application Ser. No. 10/654,668 filed Sep. 4, 2003, now U.S. Pat. No. 7,475,019 and a continuation in part of application Ser. No. 10/946,548 filed Sep. 21, 2004, now U.S. Pat. No. 7,256,708, both of which are continuations-in-part of application Ser. No. 09/443,072 filed Nov. 18, 1999, now U.S. Pat. No. 6,804,656 issued Oct. 12, 2004, which claims the benefit of U.S. Provisional Application No. 60/141,520, filed Jun. 23, 1999. The Ser. Nos. 11/072,539, 10/654,668, 10/946,548, 09/443,072, and the 60/141,520 applications are hereby incorporated by reference in their entirety for all purposes.

BACKGROUND AND SUMMARY

Embodiments relate generally to a communication system for medical applications and monitoring of equipment used in the care of monitored patients. More particularly, embodiments use a telecommunications network to facilitate the transfer of data from patient monitoring equipment into a computer system that evaluates the monitored data for medical assessment, tracking of progress of treatment, and other applications for outpatients treated from residences and residential care facilities. As used herein, a residential care facility is a facility that is equipped to provide basic housing and monitoring of residents but is not equipped to provide expert medical care. By way of illustration and not as a limitation, a residence may include a home, an apartment, an incarceration facility, a dormitory, and a condominium. A residential care facility may include a retirement home, a nursing home, and an assisted living facility.

Advances in communications, video displays, monitoring devices and computers have made it possible to remotely monitor hundreds of monitored patients from a central command center. Monitoring of patients in a hospitalized environment has become a reality. U.S. Pat. No. 6,804,656, which is incorporated by reference, describes systems and methods for providing continuous, expert network critical care services from a remote location(s) to patients located in a healthcare facility.

Various embodiments comprise a communication network for automated monitoring of patients treated in a residence or a residential care facility capable of using diverse data sources to assess the condition of such patients according to patient-specific rules. Such a network supports computerized diagnostic tools to aid caregivers in treating such patients remotely. Such a network further comprises the ability to flexibly and individually establish and/or revise alerts for patients from a central location based on individualized patient parameters and to utilize computer based algorithms to a communications network optimized for intervening appropriately.

An embodiment uses a telecommunications network to facilitate the assessment of patients receiving care in an outpatient care location (OPCL). As used herein, an outpatient care location includes residences and residential care facilities. As used herein, a residential care facility is a facility that is equipped to provide basic housing and monitoring of residents. By way of illustration and not as a limitation, a residence may include a home, an apartment, an incarceration facility, a dormitory, and a condominium. A residential care facility may include a retirement home, a nursing home, and an assisted living facility.

By way of illustration and not as a limitation, an "OPCL monitored patient" may be a patient who has an illness, an injury, or a condition that requires or would benefit from monitoring from an outpatient care location.

Patient monitoring equipment acquires monitored data elements from a patient monitoring station and transmits the monitoring data over a network to a remote command center. By way of illustration and not as a limitation, the monitoring data may be transmitted over a fiber network, a cable network, or a wireless network. Additionally, the network connection may be established over a telephone line for a period time during which data is being transferred after which the network connection may be terminated, as for example, in a dial-up session. Monitoring data comprises physiological data elements, laboratory values, symptomatology data, medication compliance data, video data elements, and audio data elements. The remote command center receives the monitoring data from all patient monitoring equipment. As used herein, the term "monitoring equipment" at least encompasses monitoring devices that reside at a bedside, monitoring devices that are worn by a patient, monitoring devices that are built into patient supporting devices (e.g., gurneys, beds, chairs, wheelchairs), monitoring devices that embedded in structures of the residential care facility (e.g., wall, floors, counters, toilets, sinks), monitoring devices that used by patients (e.g., blood pressure monitors, blood sugar monitors, lung function measurement devices (e.g., spirometers, peak flow meters), and devices the determine that the correct medications are being administered at the correct time The remote command center also accesses other data relating to the condition of a patient. By way of illustration and not as limitation, the remote command center has access to patient identifying information (name, address, marital status, age, gender, ethnicity, next of kin). A patient record datastore further comprises other data relating to the condition of a patient, for example, data relating to personal information about the patient (age, gender, ethnicity), medical history (illnesses, injuries, surgeries, allergies, medications), admissions information (symptoms, physiological data, time of admission, observations of admitting caregiver), treatment, lab data such as data that may be taken from a patient and later evaluated (such as blood work, urinalysis and other such laboratory derived information), test reports (radiology reports and microbiology reports for example), physician's notes, a patient's diagnosis, prescriptions, history, condition, laboratory results and other health-relevant data (collectively "patient data"). The data stored in the patient record datastore relevant to the patient condition, that is, the monitored data and the patient data, are collectively referred to herein as "assessment data" And may be functionally located anywhere so long as its functionality is readily available to the remote command center to allow processing of the assessment data as noted below.

DESCRIPTION OF THE FIGURES

FIG. 2 is a block diagram illustrating the flow of a patient-specific rule according to an embodiment.

DETAILED DESCRIPTION

Figure 1A:
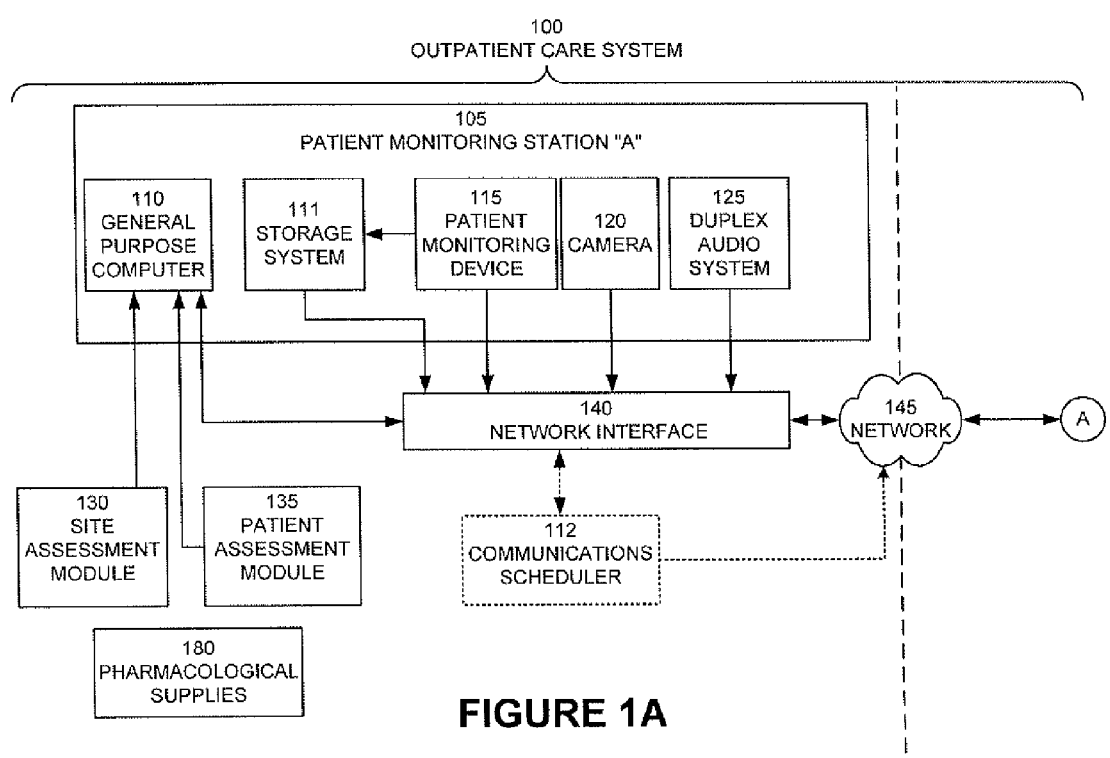
FIG. 1 is a block diagram illustrating the components of an outpatient care system according to embodiments.

The following terms used in the description that follows. The definitions are provided for clarity of understanding:

| | |
|---|---|
| assessment data - | assessment data is all data relevant to the health of a patient. |
| OPCL - | An "outpatient care location;" includes residences and residential care facilities. As used herein, a residential care facility is a facility that is equipped to provide basic housing and monitoring of residents. By way of illustration and not as a limitation, a residence may include a home, an apartment, an incarceration facility, a dormitory, and a condominium. A residential care facility may, for example, include a retirement home, a nursing home, and an assisted living facility. |
| caregiver - | an individual providing care to a patient. Examples include a nurse, a doctor, medical specialist (for example and without limitation an intensivist, cardiologist or other similar medical specialist). |
| clinical data - | data relating to the observed symptoms of a medical condition. |
| monitored data - | data received from monitoring devices connected to an OPCL monitored patient. |
| OPCL monitored patient - | an OPCL monitored patient is a patient located at an OPCL from whom monitored data is collected and whose condition is subject to assessment from a remote command center. |
| patient data - | data relating to a patient's diagnosis, prescriptions, history, condition, laboratory results and other health-relevant data. |
| physiological data - | any data relating to the functions of the human body and its processes. |
| symptom - | any sign or indication of a health condition that can be identified from patient reports and/or assessment data. |

As used herein, the term "computing device" encompasses, for example, desktop computers, laptop computers and mobile devices and other processor-equipped devices that may be developed in the future that may be configured to permit a user to interact other devices over a network. As used herein, a "mobile device" encompasses cellular telephones, personal data assistants (PDA), and smart telephones.

As used herein, a "server" is a computing device that may be configured to interact in an automated fashion with other devices over a network to serve content, web pages, and information.

An embodiment uses a telecommunications network to facilitate the assessment of patients receiving care in an outpatient care location (OPCL). As used herein, an outpatient care location includes residences and residential care facilities. As used herein, a residential care facility is a facility that is equipped to provide basic housing and monitoring of residents. By way of illustration and not as a limitation, a residence may include a home, an apartment, an incarceration facility, a dormitory, and a condominium. A residential care facility may include a retirement home, a nursing home, and an assisted living facility.

By way of illustration and not as a limitation, an "OPCL monitored patient" may be a patient who has an illness, an injury, or a condition that requires or would benefit from monitoring. The illness, condition, or injury may or may not be life threatening. The illness or condition may be chronic such that full recovery is unlikely.

In an embodiment, patient monitoring equipment acquires monitoring data from an OPCL monitored patient associated and transmits the monitoring data over a network to a remote command center. The remote command center receives the monitoring data from all of the OPCL monitored patients. The remote command center also accesses other data relating to the condition of a patient. By way of illustration and not as a limitation, the remote command center has access to patient identifying information (name, address, marital status, age, gender, ethnicity, next of kin). The patient record datastore further comprises other data relating to the condition of a patient, as for example, data relating to personal information about the patient (age, gender, ethnicity), medical history (illnesses, injuries, surgeries, allergies, medications), admissions information (symptoms, physiological data, time of admission, observations of admitting caregiver), treatment, lab data, test reports (radiology reports and microbiology reports for example), physician's notes, a patient's diagnosis, prescriptions, history, condition, laboratory results and other health-relevant data (collectively "patient data"). The data stored in the patient record datastore relevant to the patient condition, that is, the monitored data and the patient data, are collectively referred to herein as "assessment data."

In an embodiment, an outpatient care system provides care to OPCL patients based on the capabilities of the OPCL. In this embodiment, the rules engine, the decision support algorithms, the order writing software facilities and the continued care software are adapted to the capabilities of the OPCL based on the application of site assessment rules to the OPCL. In another embodiment, components of an outpatient care system may be supplied to the OPCL to improve the level of its treatment capabilities. In still another embodiment, components of the outpatient care system are packaged and assigned a site assessment code. The code is used by the remote command center to predetermine elements of the site assessment process thereby simplifying that process.

In still another embodiment, the components of the outpatient care system are determined by a rules engine based on the patient data of the OPCL patient. As the condition of the OPCL patient changes, the rules engine made revised the components the outpatient care system to add new components and/or to remove existing components from the system definition.

Figure 1B:
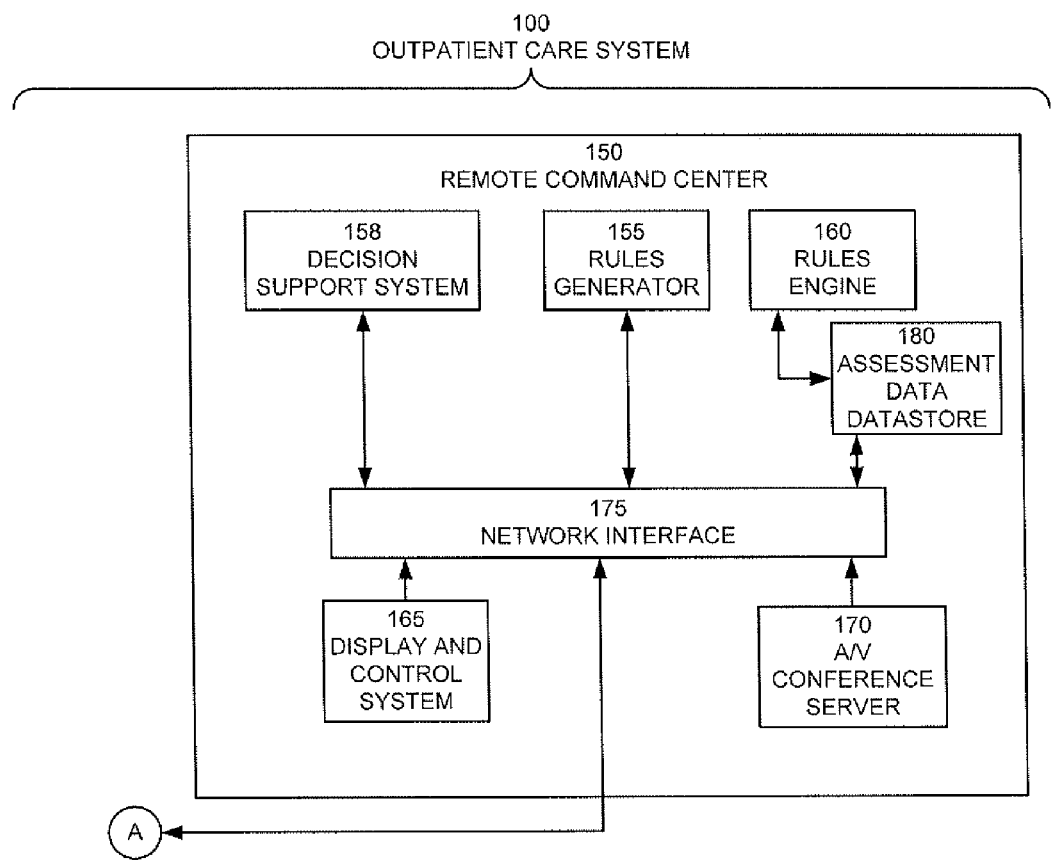

FIG. 1 is a block diagram illustrating the components of an outpatient care system according to embodiments. An outpatient care system 100 comprises a patient monitoring station "A" 105. While FIG. 1 illustrates a single patient monitoring station at a single location, the invention is not so limited. Multiple patient monitoring stations may be used from a single location. As will be explained in detail below, the outpatient care system 100 monitors a plurality of patients. Each patient is thus associated with a patient monitoring station. For the sake of clarity, the description that follows will refer to the patient monitoring station "A" 105. However, the description applies to all patient monitoring stations within the outpatient care system 100.

The patient monitoring station "A" 105 comprises a general purpose computer 110, a storage system 111, a patient monitoring device 115, a camera 120, and a duplex audio system 125. While FIG. 1 illustrates a patient monitoring device, the invention is not so limited. Multiple patient monitoring devices may be used without departing from the scope hereof. For the sake of clarity, the description that follows will refer to patient monitoring device 115.

The general purpose computer 110 provides data entry, display and printing capabilities through means known to those skilled in the art. The general purpose computer 110 further executes software instructions that cause the general purpose computer 110 to perform the functions as described herein.

The components of the patient monitoring station "A" 105 are connected to a network 145 via network an interface 140. The network 145 may be a wired network, a wireless network, a satellite network, a public switched telephone network, an IP network, a packet switched network, a cell phone network, a cable network, and a coax network, a hybrid fiber coax network.

In an embodiment, an optional site assessment module 130 and a patient assessment module 135 connect to the network interface 140 via the general purpose computer 110.

The patient monitoring device 115 acquires physiological data from a patient in real-time. In an embodiment, the general purpose computer 110 comprises a printer that receives and prints orders and instructions from an authorized remote caregiver. By way of illustration and not as a limitation, an order comprises a lab order, a medication, and a procedure. The orders are tailored to the capabilities of the OPCL patient care system 100.

A network interface 140 provides access to the network 145 for transmission of the monitored data, video signal, and audio signals to the remote command center 125 and the receipt of the audio signals and, optionally, printer signals at the monitoring station.

It is anticipated that the outpatient care system 100 will be used in OPCLs that have limited resources. The optional site assessment module 130 provides information indicative of the ability of an OPCL to provide monitoring data via the network interface 140. In an embodiment, the site assessment module acquires the site assessment data from the OPCL and produces service level measures comprising an inventory of the available monitoring data elements. These data may be acquired via a survey of the particular location.

In yet another embodiment, some or all of the specific components of the outpatient care system 100 are determined by a rules engine and are provided to the OPCL. By way of illustration and not as a limitation, the rules engine may determine that an out patient suffering from heart disease requires a portable heart monitor the measures parameters relating to heart function.

In another embodiment, when an outpatient care system 100 is provided to an OPCL, the outpatient care system 100 comprises an assessment code that details the capability of the outpatient care system 100. By way of illustration and not as a limitation, the assessment code may indicate the number of the monitoring devices incorporated into the outpatient care system 100, the patient parameters that can be acquired using the monitoring devices, and the pharmacological supplies 180 provided with the outpatient care system 100.

Also connected to the network 145 is the remote command center 150. The remote command center 150 comprises a patient rules generator 155, a rules engine 160, decision support system 158, a display and control system 165, an audio/video (A/V) conferencing server 170, and an assessment data datastore 180. The decision support system 158 issues instructions to the rules generator 155 when rules are required for a patient. Once the rules are generated by the rules generator 155, the decision support system 158 causes the rule to be referred to the rules engine 160 for subsequent application to the specific patient for whom the rule was originally generated. A network interface 175 provides connectivity between the network 145 and the other elements of the remote command center. The network 145 is configured to permit access to external networks (not illustrated), such as the Internet.

The video camera 120 is movable both horizontally and vertically and zoomable through remote commands from the display and control system 165 of the remote command center 150 so that specific views of the patient may be obtained both up close and generally. The duplex audio system 125 comprises a speaker and microphone (not illustrated) to permit both one-way audio monitoring of the patient and two-way communication with the patient or others in proximity to the patient monitoring station "A" 105.

The remote command center 125 receives monitored data from the patient monitoring station "A" 105 via the network 145 through the network interface 175. The monitored data comprises real-time data received from monitoring equipment at the patient monitoring station "A" 105 that is configured to receive the physiological data from an OPCL monitored patient associated with the patient monitoring station "A" 105.

Remote command center 125 further comprises an assessment data datastore 180. The assessment data datastore 180 receives the monitoring data and also receives the patient data via the network 145. The patient data may be received from various sources (not illustrated), including by way of example, doctors offices, laboratories, and healthcare facilities. The assessment data datastore 180 as illustrated herein is a logical function that in various embodiments may be co-located with the remote command center or may be located apart from the remote command center but connected to the remote command center via a network so as to serve the functions required to support the continuous evaluation and assessment of patients at the remote command center.

While FIG. 1 illustrates the components of an OPCL monitored outpatient care system 100 for a single patient, the outpatient care system 100 is not so limited. In operation, a plurality of outpatient care systems 100 will "continuously" monitor the condition of a plurality of outpatients in accordance with the requirements of the patient-specific rules established for each patient. "Continuously" is this context means that OPCL monitored outpatient care system 100 is in a ready state to receive data from monitored patients and to apply patient-specific rules in accordance with the requirement of those rules. An individual patient-specific rule may, for example, require that data for that particular patient be evaluated on a scheduled basis, each time new data arrives, or based on a condition that depends on previous assessments of the assessment data. Thus, the outpatient care system 100 may be characterized as operating continuously even though the system may not be processing data for any particular patient at a particular moment in time.

The rules generator 155 and the rules engine 160 facilitate automated detection of impending problems thereby allowing for intervention before a patient condition reaches a crisis state. The rules generator 155 and the rules engine 160 also provided automated evaluation of the condition of a patient to determine whether changes in the patient's condition warrant changes in the patient's treatment plan. (this could be to contact the patient, family member or an ambulance, etc).

The rules engine generator 155 establishes one or more rules for the OPCL monitored patient associated with the patient monitoring station "A" 105. In an embodiment, the rules generator 155 generates a patient-specific rule that is consistent with the patient assessment data and with the service level measures established by the site assessment module 130. The rules engine 160 applies a patient-specific rule to selected data elements of patient assessment data (assessment data is all data relevant to the health of a patient) obtained from the datastore 180 to determine in an automated fashion whether the conditions of the patient-specific rule for an OPCL monitored patient has been satisfied. In the event the patient-specific rule has been satisfied, the remote command center determines in an automated fashion and in accordance with the rule the action to be taken. By way of illustration and not as a limitation, the action taken may be in the form of an alert that intervention with the patient is warranted or that the patient's treatment plan should be changed. Alternatively, the "action" in response to satisfying the conditions of the rule may be to maintain the monitoring of the patient without issuing an alert.

In one embodiment, conditions of a patient-specific rule are established to determine whether a patient's condition is deteriorating, improving or stable. The patient-specific rule may also establish conditions for taking a specific action. For example, if the patient's condition is deteriorating, the rule may establish that an action to be taken is the issuance of an alert comprising an intervention order and protocol. In another embodiment, the conditions of the patient-specific rule may determine whether an OPCL monitored patient requires monitoring by a monitoring station. If not, the rule may establish that the action to be taken is the issuance of a release protocol and order. In still another embodiment, a patient-specific rule dictates threshold limits for changes over time of specific vital sign data. Thresholds that are patient-specific disease-specific are established. The rules engine then evaluates the monitored data for the specific vital sign data to determine if a change threshold has been exceeded.

For example, a patient with coronary artery disease can develop myocardial ischemia with relatively minor increases in heart rate. Heart rate thresholds for patients with active ischemia (e.g. those with unstable angina in a coronary care unit) are set to detect an absolute heart rate of 75 beats per minute. In contrast, patients with a history of coronary artery disease in a surgical ICU have thresholds set to detect either an absolute heart rate of 95 beats per minute or a 20% increase in heart rate over the baseline. For this threshold, current heart rate, calculated each minute based on the median value over the preceding 5 minutes, is compared each minute to the baseline value (the median value over the preceding 4 hours).

In another embodiment, a patient-specific rule is based on multiple variables. The following example illustrates a multi-variable patient-specific rule directed to assessing a patient with a heart condition. In this embodiment, a patient-specific rule utilizes an algorithm that takes as input vital signs (for example, weight, blood pressure, heart rate and SpO2) and symptoms (for example, shortness of breath or "SOB", fatigue, breathlessness, arrhythmias read of from RSR). The algorithm utilizes baseline values for each of the physiologic variables. In an embodiment, the output of the algorithm is expressed a single score that determines an action to be taken with respect to the patient. In another embodiment, the action is based on the patient's New York Heart Association (NYHA) heart failure classification-separate algorithm for Class II, III and IV. The patent's failure classification may be displayed as a color-coded alert at the remote command center. In an embodiment, the algorithm is defined to yield an output for any combination of input signs and symptoms, including missing values.

FIG. 2 is a block diagram illustrating the flow of a multi-variable patient-specific rule according to an embodiment. Assessment data elements are evaluated using tables that are specific to one of the assessment data elements. As illustrated in FIG. 2, the weight change data elements 202 are evaluated according to Tables 1A and 1B, blood pressure change data elements 204 are evaluated according to Tables 2A and 2B the heart rate change data elements 206 are evaluated according to Tables 3A and 3B, the $O_2$ saturation change data elements 208 are evaluated according to Table 4, the symptoms change data elements 210 are evaluated according to Tables 5, 6, and 7, and the rhythm strip data elements 212 are evaluated according to Table 8. The results of the evaluations of Tables 1-8 (elements 214-224) are evaluated in accordance with Table 9. The results of Tables 1-7 are evaluated to produce a consolidated score. The consolidated score 226 is then evaluated using Table 10 to determine an action to be taken with respect to the outpatient associated with the evaluated assessment data elements.

The algorithm may include the following steps:

Discretization of the input variables: This means that changes in the input variables are not taken as raw values (e.g. change in SpO2 from 96% to 91%) but translated into a range of discrete scores. These scores range from −1 to 10, where −1 encodes a missing value (no measurement) and positive scores describe different grades of adverse changes (10 encoding for the most adverse development). The discretization step serves to make the problem manageable and to limit the different combinations of signs and symptoms. More levels of discretization (3 levels are illustrated) mean a more complex algorithm. The discretization is described in Tables 1 To 8.

Scoring of sign and symptom combinations: There are different possibilities of scoring the sign and symptom combinations. In this algorithm, the addition of all score points into a total score is chosen. This step and the prescription how to handle missing data in the scoring of combinations, is described in Table 9.

Total score and recommended action: The total score of the sign and symptom combination as computed from Table 9 is translated into a color-coded alert state, linked to a recommended action for the nurse operating the data review application. This step is encoded in Table 10.

The following tables apply to the discretization of signs and symptoms. For Tables 1 to 5 there are two ways the input is used: Day-to-day changes and longer term trends; the output is the highest applicable score depending if daily change or trend score is higher. The tables are constructed such that there is a defined output for all situations of input daily changes or trends deliver defined results. Daily changes are relative to the baseline data (except for weight, which is based on daily changes). Trends are given in absolute terms.

TABLE 1

Weight Change

A: Weight Increase

| Daily Increase | Trend (X3 days) | Output |
| --- | --- | --- |
| >3 lb from day before | >2 kg | 3 |
| 2-3 lb from day before | 1-2 kg | 2 |
| <2 lb from day before | <1 kg | 0 |
| Missing data | | −1 |

B: Weight Decrease

| Daily Decrease | Trend | Output |
| --- | --- | --- |
| >2 kg | | 2 |
| <=2 kg | | 0 |
| Missing data | | −1 |

TABLE 2

Blood Pressure Change (from baseline)

A: Blood Pressure Increase

| Daily Increase | Trend (X7 days) | Output |
| --- | --- | --- |
| >30 mm Hg from baseline | Mean of systolic > 20 mm Hg from baseline | 3 |
| 15-30 mm Hg from baseline | Mean systolic 10-20 mm from baseline | 2 |
| <15 mm Hg from baseline | Mean systolic < 10 mm from baseline | 0 |
| Missing data | | −1 |

B: Blood Pressure Decrease

| Daily Decrease | Absolute values | Output |
| --- | --- | --- |
| >20 mm Hg from baseline (systolic or diastolic) | Systolic < 90 mm Hg or diastolic < 40 mm Hg | 3 |
| 10-20 mm Hg from baseline (systolic or diastolic) | Systolic 90-110 mm Hg or diastolic 40-50 mmm Hg | 2 |
| <10 mm Hg from baseline (systolic or diastolic) | Systolic > 110 mm Hg and diastolic > 50 mm Hg | 0 |
| Missing data | | −1 |

TABLE 3

Heart Rate Change

A: Heart Rate Increase

| Daily Increase | Absolute values | Output |
| --- | --- | --- |
| >20% from baseline | >110 | 3 |
| 10-20% from baseline | 90-110 | 2 |
| <10% from baseline | <90 | 0 |
| Missing data | | −1 |

TABLE 3-continued

Heart Rate Change

B; Heart Rate Decrease

| Daily Decrease | Absolute values | Output |
| --- | --- | --- |
| >20% from baseline | <50 | 3 |
| 10-20% from baseline | 50-60 | 2 |
| <10% from baseline | >60 | 0 |
| Missing data | | −1 |

TABLE 4

O2 Sat Decrease (from baseline) brian updates should be an AND % O2 Sat Decrease

| Absolute Daily Decrease | Absolute values | Output |
| --- | --- | --- |
| >5% from baseline | <91% | 3 |
| 3-5% from baseline | <=93% | 1 |
| <3% from baseline | >93% | 0 |
| Missing data | | −1 |

TABLE 5

Shortness of breath
Symptoms Increase

| Shortness of breath | Output |
| --- | --- |
| Much worse than day before | 10 |
| Somewhat worse than day before | 5 |
| No change | 0 |
| Missing data | −1 |

TABLE 6

Fatigue

| Fatigue | Output |
| --- | --- |
| Much worse | 3 |
| Somewhat worse | 2 |
| No change | 0 |
| Missing data | −1 |

TABLE 7

Swelling (edema)

| Swelling (edema) | Output |
| --- | --- |
| Much worse | 7 |
| Somewhat worse | 3 |
| No change | 0 |
| Missing data | −1 |

TABLE 8

Rhythm strip premature ventricular contractions
(pvc) >3 per min gets 5 points

| Rhythm | Output |
| --- | --- |
| New AF or >= 3 bit runs of ventricular rhythm in a row (ventricular ectropy) | 10 |
| PVCs >= 10 per minute | 5 |
| No change | 0 |
| Missing data | −1 |

TABLE 9

Scoring

| CONDITION | ACTION |
|---|---|
| If (output of Table 8 = 10) | then output of table 10 = red |
| Else if (output from Tables 1-8 is −1 in more than 1 case) | then output of Table 10 = yellow |
| Else { | |
| Score_total = | sum of all outputs of Tables 1 to 7 unless those are −1 |
| Max_total = | sum of all maximum output from Tables 1 to 7 where output is not −1 |
| Score_normal = } | score_total/max_total |

Score_normal has a value between 0 and 1 in all cases, also when 1 data point is missing.

TABLE 10

Response

| Score_normal | Output | Description |
|---|---|---|
| 0-0.2 | Green | Stable continue to monitor |
| 0.2-0.5 or more than 2 missing data | Yellow | Retake vital signs. Troubleshoot for technique. Check timing on when meds were taken If the values continue to be out of range −> Check if RN visit scheduled. If rhythm change call MD |
| 0.5-0.75 | Orange | Call patient on the phone to repeat measurements for validation. Check if RN visits planned. Check standing orders Call MD |
| >0.75 or arrhythmias | Red | Call patient Check standing orders Call case manager, caregiver and MD Prepare for triage to ER |

In an embodiment, all of the symptoms are acquired together in one questionnaire. So either all data on symptoms are present, if the patient filled in the questionnaire, or no data for any of the three symptoms. Since more that one missing data point is defined to lead to calling the patient and not using the alert scheme, missing symptom questionnaires result in call to the patient.

For multi-variable patient-specific rules, thresholds rely on known or learned associations between changes in multiple variables, which variables may comprise diverse data types. Thus, a patient-specific rule may associate monitored physiological data with patient clinical data. The association may change depending on the diagnosis of the patient, the medication given the patient, and the results of laboratory data. For example, a patient-specific rule may associate central venous pressure and urine output, because simultaneous decreases in these two variables can indicate that a patient is developing hypovolemia. Another patient-specific rule may cause the rules engine to evaluate laboratory data (e.g. looking for need to exclude active bleeding and possibly to administer blood).

In an embodiment, a patient-specific rule is established for an OPCL monitored patient and the OPCL monitored patient is associated with a particular outpatient monitoring station. In this embodiment, if the patient were later associated with a different monitoring station, such as a monitoring station in a physician's office, the remote command center would associate the patient-specific rule with the different monitoring station at the time that the association between the OPCL monitored patient and the different monitoring station is made. In this way, patient-specific rules "move" with the patient without manual intervention.

In another embodiment, the patient monitoring equipment acquires the monitored data elements from a patient monitoring station and stores monitoring data in storage system 111. The stored monitoring data is sent (pushed) from the storage system 111 to the remote command center 150 along with the patient data under control of an optional communications scheduler 112 at a pre-established time such as hour or when an "event" occurs as noted below, or when requested by remote command center 150. The communications scheduler 112 may be configured via the network 145. In an embodiment, the configuration of communications scheduler 112 is automatically performed by the remote command center 150 in response to the rules engine 160. Thus, if the evaluation of the patient monitoring data by the rules engine 160 determines that the patient's condition has or may be changing, the rules engine may direct the remote command center 150 to revise the configuration of communications scheduler 112 to report the stored patient monitoring data more or less often as appropriate under the circumstances.

A patient-specific rule may be established for determining the proper dosing of a outpatient. The following example illustrates a patient-specific rule directed to determining the dosing a heart patient prescribe the drug warfarin. As used in the following example, international normalized ratio (INR) are measures of the extrinsic pathway of coagulation and are used to determine the clotting tendency of blood. The normal range for the INR is 0.8-1.2.

Figure 6:
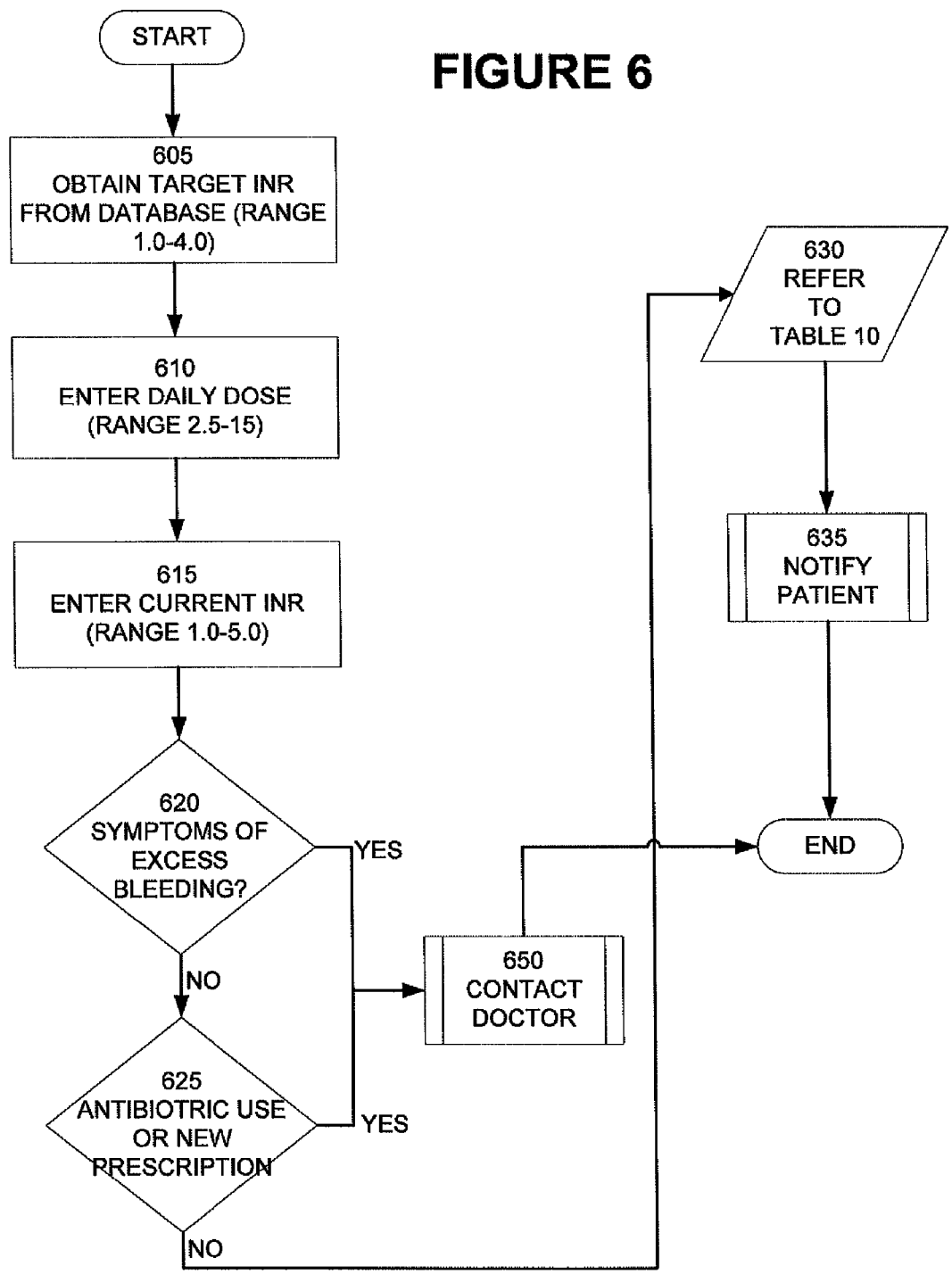
FIG. 6 is a block diagram illustrating a flow of a weekly warfin (Coumadin) dosing check according to an embodiment.

FIG. 6 is a block diagram illustrating a flow of a weekly warfin (Coumadin) dosing check according to an embodiment. A target INR for an outpatient is obtained 705. A daily dosage of the outpatient is entered 710. A current INR of the outpatient is entered 715. A determination is made whether the outpatient has any symptoms of excess bleeding 720. By way of illustration and not by way of limitation, systems of excess bleeding may include black stools and bleeding gums. If the outpatient has any symptoms of excess bleeding, the outpatient's physician is contacted 750.

When the outpatient does not have any symptoms of excess bleeding, a determination is may whether the outpatient has used any antibiotics or new prescriptions within the last two weeks 725. When the outpatient has used antibiotics or started a new prescription within the last two weeks, the outpatient's physician is contacted 750.

In an embodiment, data required to determine the appropriate warfin dosing may be obtained from a database, from a healthcare provider, and/or from the outpatient.

When the outpatient has not used antibiotics or started a new prescription within the last two weeks, the information inputted for the outpatient is evaluated to locate and select a cell from one of the appropriate sub-tables of Table 11 730. The sub-tables of Table 11 are set forth below.

Based on the content of the cell, dosing advice may be provided to the outpatient 735. For example, when the content of the selected cell is "hold", the dosing advice may be, "Do not take your warfin today." When the content of the select cell is "hold and call", the dosing advice may be, "Do not take your warfin and call your physician for further advice." When the when the content of the selected cell includes an asterisk (*), the dosing advise may be "Recheck your INR in 48 hours." When the when the content of the selected cell includes a double asterisk (**), the following message may be added: "Recheck your INR in 24 hours." After two consecutive entries with outputs of hold, the following message may be added: "Call your physician for further advice."

TABLE 11

| CUR-RENT INR | TARGET INR | | | | |
|---|---|---|---|---|---|
| | 1-1.49 | 1.5-1.99 | 2-2.49 | 2.5-3 | 2.0-3.0 | 2.5-3.5 |
| Sub-Table For Dose 2.5 mg | | | | | | |
| <1.5 | 2.5 | 5 | 10 | 15 | 10 | 15 |
| 1.5-1.99 | Hold | 2.5 | 5 | 5 | 10 | 10 |
| 2-2.49 | Hold | Hold | 2.5 | 2.5 | 2.5 | 5 |
| 2.5-3.0 | Hold & call | Hold | 2.5 | 2.5 | 2.5 | 2.5 |
| 3.1-4.0 | Hold & Call | Hold & Call | Hold | Hold | Hold | 2.5 |
| >4 | Hold & Call | Hold & Call | Hold & Call | Hold** | Hold** | Hold* |
| Sub-Table For Dose 5 mg | | | | | | |
| <1.5 | 5 | 10 | 10 | 10 | 10* | 10* |
| 1.5-1.99 | Hold | 5 | 7.5 | 10 | 10 | 10* |
| 2-2.49 | Hold | Hold | 5 | 5 | 5 | 7.5 |
| 2.5-3.0 | Hold & call | Hold | 5 | 5 | 5 | 5 |
| 3.1-4.0 | Hold & Call | Hold & Call | Hold* | Hold* | Hold* | 5 |
| >4 | Hold & Call | Hold & Call | Hold & Call | Hold** | Hold** | Hold* |
| Sub-Table For Dose 7.5 mg | | | | | | |
| <1.5 | 7.5 | 10 | 10 | 12.5* | 12.5* | 15* |
| 1.5-1.99 | 5 | 7.5 | 7.5 | 10 | 10 | 10 |
| 2-2.49 | Hold | Hold | 7.5 | 10 | 7.5 | 10 |
| 2.5-3.0 | Hold & call | Hold | 7.5 | 7.5 | 7.5 | 10 |
| 3.1-4.0 | Hold & Call | Hold & Call | Hold | Hold | Hold | Hold |
| >4 | Hold & Call | Hold & Call | Hold & Call | Hold** | Hold** | Hold* |
| Sub-Table For Dose 10 mg | | | | | | |
| <1.5 | 10 | 12.5 | 15 | 15* | 15* | 15* |
| 1.5-1.99 | 5 | 10 | 12.5 | 15* | 12.5 | 15* |
| 2-2.49 | Hold | Hold | 10 | 12.5 | 10 | 12.5 |
| 2.5-3.0 | Hold & call | Hold | 10 | 10 | 10 | 12.5 |
| 3.1-4.0 | Hold & Call | Hold & Call | Hold | Hold | Hold | 7.5 |
| >4 | Hold & Call | Hold & Call | Hold & Call | Hold** | Hold** | Hold* |
| Sub-Table For Dose 12.5 mg | | | | | | |
| <1.5 | 12.5 | 15 | 15 | 15* | 15* | 20* |
| 1.5-1.99 | 7.5 | 12.5 | 15 | 15* | 15* | 15* |
| 2-2.49 | Hold | Hold | 12.5 | 15 | 12.5 | 15* |
| 2.5-3.0 | Hold & call | Hold | 10 | 12.5 | 12.5 | 12.5 |
| 3.1-4.0 | Hold & Call | Hold & Call | Hold* | Hold | Hold | 10 |
| >4 | Hold & Call | Hold & Call | Hold & Call | Hold** | Hold** | Hold* |
| Sub-Table For Dose 15 mg | | | | | | |
| <1.5 | 15 | 20 | 20 | 20* | 20* | 20* |
| 1.5-1.99 | 10 | 15 | 20 | 20* | 20* | 20* |
| 2-2.49 | Hold | Hold | 15 | 17.5 | 15 | 20* |
| 2.5-3.0 | Hold & call | Hold | 12.5 | 15 | 15 | 15 |
| 3.1-4.0 | Hold & Call | Hold & Call | Hold* | Hold | Hold | 15 |
| >4 | Hold & Call | Hold & Call | Hold & Call | Hold** | Hold** | Hold* |

The remote command center 150 evaluates the "delayed" monitored data and assessment data in the same manner as if these data were received in real time. By way of illustration, the remote command center will generate patient-specific rules using the rules generator 155, apply those rules using the rules engine 160 to the delayed monitored data and patient data and provide guidance to the OPCL. The decision support algorithms of the decision support system 158 may also be applied to the delayed monitored data and patient data. This embodiment thus provides high quality care in environments where continuous high bandwidth communications are not available or economically infeasible.

In still another embodiment, the delivery of stored monitoring data and patient data is expedited by an urgent consultation warning system (herein, the UCWS) operated by general purpose computer 110. The UCWS evaluates the monitoring data and patient data before those data are stored in the storage system 111 to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the remote command center 150 for evaluation.

In another embodiment, the remote command center 150 may poll the storage system 111 for patient monitoring data by sending a command to the communications scheduler 112 via the network 145. In this embodiment, the remote command center 150 may poll the storage system 111 on a scheduled basis as well as a "need" basis as determined by the rules engine 160. Thus, if the evaluation of the patient monitoring data by the rules engine determines that the patient's condition has or may be changing, the rules engine may directed the remote command center 150 to poll the storage system 111 more or less often as appropriate under the circumstances.

Figure 3:
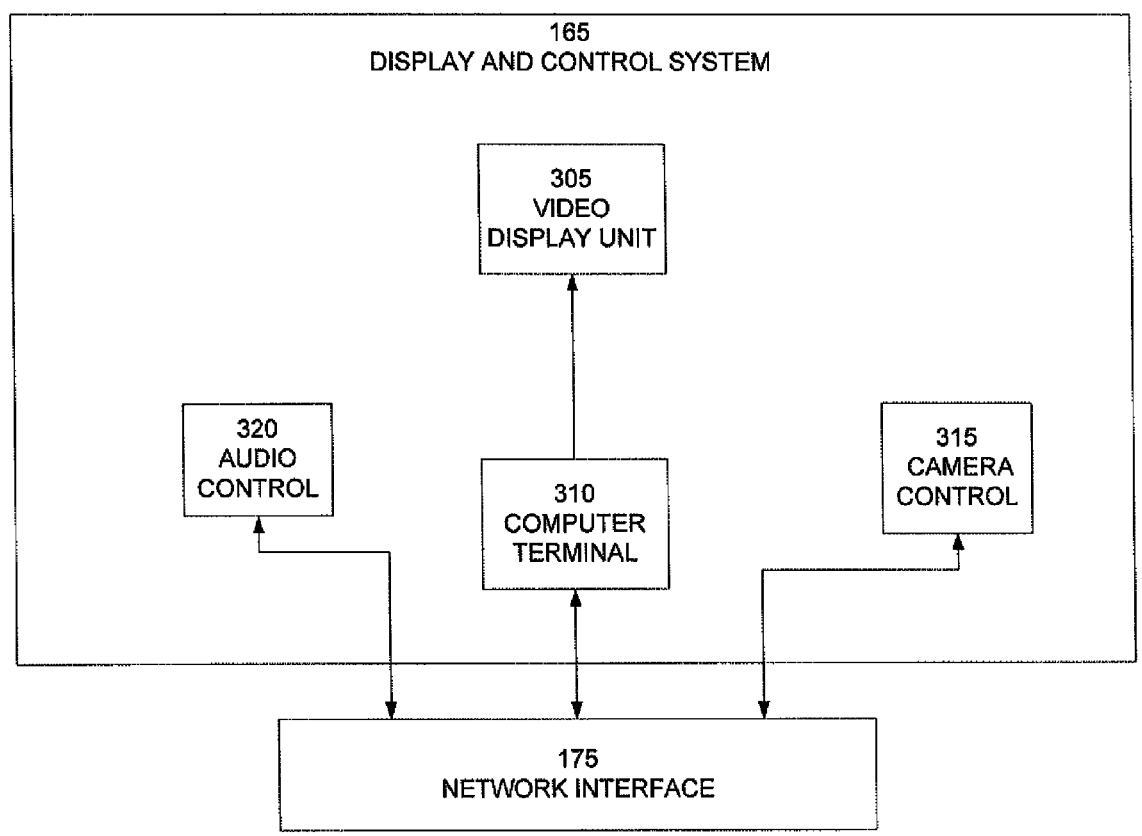
FIG. 3 is a block diagram illustrating a display and control system according to an embodiment.

Referring to FIG. 1, the display and control system 165 provides the human interface for the remote command center. FIG. 3 is a block diagram illustrating a display and control system according to an embodiment. A display and control system 165 comprises a video display unit 305, a computer terminal 310, a camera control 315, and an audio control 320. The video display unit 305 displays real-time monitoring data and video images from the patient monitoring station "A" 105. The computer terminal 310 allows selecting the layout and content displayed on the video display unit 305, provides access to the record of the patient associated with the patient monitoring station "A" 105, and permits entry of data into that record. The camera control 315 permits control from the remote command center 125 of the video camera 120 (see FIG. 1) at the patient monitoring station "A" 105. The audio control permits control from the remote command center 150 of a microphone and a speaker within the duplex audio system 125 of patient monitoring station "A" 105. Connectivity between the components of the display and control systems 165 and the patient monitoring station "A" 105 is provided by the network interface 175, the network 145, and the network interface 140.

Figure 4:
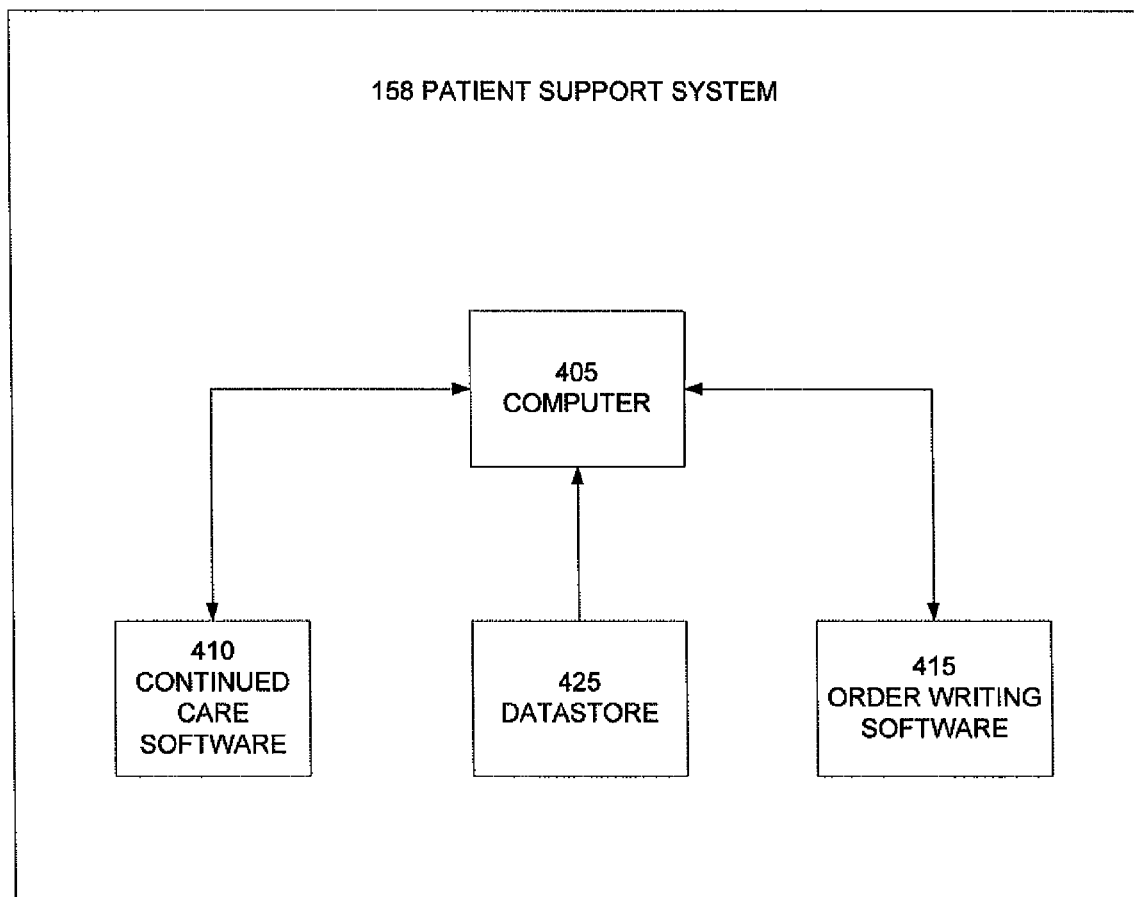
FIG. 4 is a block diagram illustrating a decision support system according to an embodiment.

Referring again to FIG. 1, the remote command center 150 comprises decision support system 158. FIG. 4 is a block diagram illustrating a decision support system according to an embodiment. Referring to FIG. 4, decision support system 158 is connected to a network interface 175 and comprises a computer 405. The computer 405 operates continued care software 420 and order writing software 415. The continued care software 410 and the order writing software 415 make calls to the datastore 425 to access the assessment data related to a particular OPCL monitored patient associated with the patient monitoring station "A" 105 (see, FIG. 1).

The continued care software 420 comprises decision support algorithms that operate on elements of assessment data and/or input from a caregiver to facilitate decisions relating to diagnosis, treatment and triage. The continued care software may be applied at the time the patient is admitted and throughout the patient's stay within a treatment facility. Thus, a diagnosis may be made based on the initial data acquired during admission, following the completion of laboratory procedures, or after other pertinent information is acquired. In an embodiment, the continued care software 420 evaluates selected data elements of assessment data in accordance with the requirements of the algorithm and provides an alert if those data are indicative of a different diagnosis. The alert may take the form of suggested diagnoses that are vetted by a series of questions posed by the continued care software 420 to a caregiver. Based on the responses to the questions, a suggested diagnosis may be eliminated. The alert may also comprise instructions for specific tests to be run on the OPCL monitored patient to help formulate a new diagnosis. Once a diagnosis is confirmed, the continued care software 420 continues to monitor changes in patient data and issues an alert if the current diagnosis should be reevaluated by a caregiver.

The decision support system 158 also issues instructions to the rules generator 155 when rules are required for a patient. Once the rules are generated by the rules generator 155, the decision support system 158 causes the rule to be referred to the rules engine 160 for subsequent application to the specific patient for whom the rule was originally generated.

In another embodiment, the patient monitoring equipment acquires monitored data elements from a patient monitoring station and stores the monitoring data in the general purpose computer 110. The stored monitoring data is sent from the general purpose computer 110 to the remote command center 150 along with patient data under control of an optional communications scheduler 112 at a pre-established time such as hour or when an "event" occurs as noted below, or when requested by the remote command center 150. The continued care decision support system 158 evaluates selected data elements of the assessment data in the same manner as if these data were received in real time and provides an alert if those data are indicative of a different diagnosis.

In still another embodiment, the delivery of stored monitoring data and patient data is expedited by an urgent consultation warning system (herein, the UCWS) operated by the general purpose computer 110. The UCWS evaluates the monitoring data and patient data before those data are stored to determine if an event has occurred that warrants an urgent consultation. By way of illustration and not as a limitation, changes in hemodynamic and respiratory measures over time indicative of a degrading condition of a patient would trigger an immediate reporting of all stored monitored and patient data to the decision support system 158 for evaluation.

In still another embodiment, the continued care software 420 operates on a diagnosis to "triage" a patient. For example and without limitation a caregiver requests an Apache II score based on the diagnosis. The continued care software 420 calls selected data elements from the datastore 425 appropriate to the diagnosis. The values of the selected data elements are weighted according to an algorithm and a patient severity score is determined. This patient severity score is used to determine whether the patient is treated in a patient monitoring station. For example, if one embodiment, if the severity score is greater than or equal to a particular threshold, the patient is identified as requiring observation via a patient monitoring station. If the severity score is less than that threshold, the patient is triaged to a facility other than a patient monitoring station, thereby assigning the patient monitoring stations to patients who are most likely to benefit from monitoring and continued assessment.

In another embodiment, the computer 405 operates the order writing software 415, either independently or in conjunction with the operation of the continued care software 420 to order tests to complete the data required for a potential diagnosis. In an embodiment, the order writing software 415 may communicate orders to a primary healthcare facility (e.g., a hospital or clinic). In another embodiment, the order writing software 415 may selectively communicate order to a pharmacy associated with the outpatient. For example, an order for an blood test or X-ray may be communicated to a primary healthcare facility and a prescription may be communicated to the outpatient's pharmacy.

According to another embodiment, the orders issued by the order writing software 415 are consistent with the service level measures established by the site assessment module 130.

Figure 5:
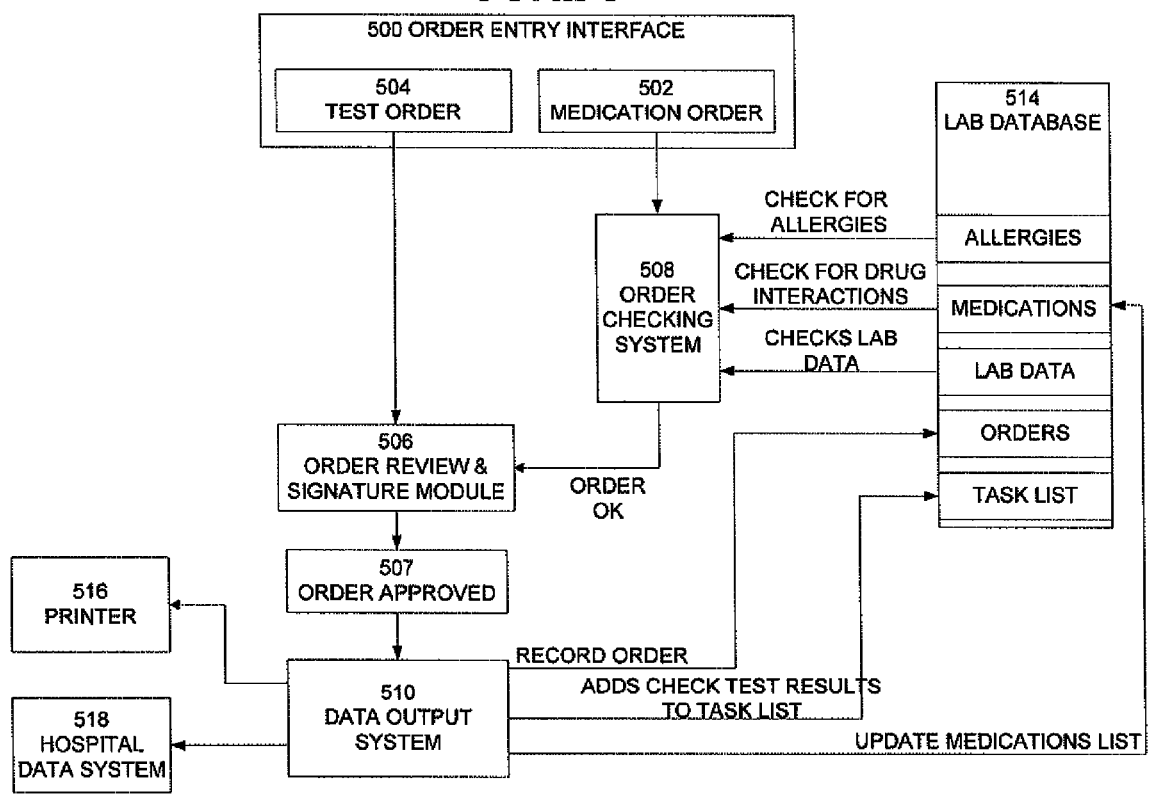
FIG. 5 is a block diagram illustrating an order writing data flow according to an embodiment.

FIG. 5 is a block diagram illustrating an order writing data flow according to an embodiment. Referring to FIG. 5, an order entry user interface 500 allows the caregiver to order procedures and medication to assist the patients at a patient monitoring station. For example, the caregiver can order an ECG 504. Thereafter the order is reviewed and a digital signature relating to the caregiver is supplied 506. Once reviewed and signed off, the order is approved 507 and sent to the data output system 510. Thereafter the data output system prints the order to the printer at a patient monitoring station 516. For record keeping purposes the order is exported in the HL7 language to the hospital data system 518. In addition the data output system adds an item to the database that will subsequently cause a caregiver to check the ECG results. This notification to the task list is provided to the database 514. In addition, as part of the database an orders file relating to the specific patient is also kept. The fact that an ECG has been ordered is entered in the orders file for that patient.

In a similar fashion using the order entry user interface 500 the caregiver can order medications 502 for a patient. The medication order then is provided to an order checking system 508. The order checking system retrieves information from the database 514 relating to allergies of the patient and medication list that comprises medications that are already being administered to the patient. This allows for the order checking system to check for drug allergies and drug interactions. Further laboratory data is extracted from the database 514 and the order checking system checks to insure that there will be no adverse impact of the recommended dosage upon the renal function of the patient. Once the order checking system 508 is completed, the order is approved and provided to the order review and signature module 506. In this module the digital signature of a caregiver is affixed to the order electronically and the order is approved 507. Thereafter it is provided to the data output system 510 where again the orders are printed or transmitted via HL7 for the patient monitoring station 516, for the pharmacy 517 and for the treatment facility data system 518. In this case, any medications that are ordered are then provided to the medications list file in the database 514 so that the complete list of all medications that are being administered to the patient is current.

In an embodiment, the order checking system 508 determines whether the order is consistent with the service level measures established by the site assessment module 130. If the order is not consistent with the service level measures, the order is suppressed and the caregiver is notified that an alternative treatment is required.

As noted, the order writing software 415 may also interact with the continued care software 410. Referring again to FIG. 4, a caregiver selects a suggested diagnosis from the continued care software 420 and enters the order writing software 415. As previously described, the orders issued by the order writing software 415 are consistent with the service level measures established by the site assessment module 130. The order writing software 415 identifies the appropriate test or tests and issues the actual order or orders for the identified tests. Each order is then sent to the appropriate testing facility. The tests are conducted, and the completion of the order is reported to the data store 425 and the completion information is received by the order writing software 415. Additionally, continued care software 420 acquires the test results from the datastore 425 and updates the list of suggested diagnoses.

The continued care software 420 provides reference material directed to the standardized treatment of the OPCL monitored patient. In order to standardize treatment provided to OPCL monitored patients at the highest possible level, decision support algorithms are used in the present invention. These include textural material describing the topic, scientific treatments and possible complications. This information is available in real time to assist in all types of clinical decisions from diagnosis to treatment to triage.

In an embodiment, the decision response algorithms are responsive to the service level measures established by the site assessment module 130. In this embodiment, the algorithms adjust the response to fit the capabilities of the OPCL.

As noted earlier, an aspect is to standardize care and treatment across patient monitoring stations. This is effective in the present invention by providing decision support to caregivers as well as information concerning the latest care and practice standards for any given condition. Table 12 below is an exemplary list of a wide variety of conditions within the general categories of cardiovascular, endocrinology, general, gastrointestinal, hematology, infectious diseases, neurology, pharmacology, pulmonary, renal, surgery, toxicology, for which algorithms of care have been developed and which are particularly suited for care of outpatients. As will be appreciated by those skilled in the art, the list in Table 12 is not exhaustive and other decision support algorithms may be developed for other conditions without departing from the scope hereof.

TABLE 12

Bradyarrhythmias diagnosis & treatment
Congestive heart failure diagnosis & treatment
Fluid resuscitation indications & treatment
Myocardial infarction diagnosis & treatment
MI with left bundle branch block diagnosis
Pulmonary embolism diagnosis
Supra-ventricular tachyarrhythmias diagnosis & treatments
Unstable angina diagnosis & treatment
Venous thromboembolism prophylaxis treatment
Venous thrombosis: diagnosis & treatment
Ventricular arrhythmias diagnosis & treatment
Warfarin treatment
Pneumonia, community acquired diagnosis and treatment
Asthma diagnosis & treatment
Chronic Obstructive Pulmonary Disease diagnosis and treatment
Diuretic treatment
Hyperkalemia: diagnosis & treatment
Hypernatremia: diagnosis & treatment
Hypokalemia: diagnosis & treatment
Hyponatremia: diagnosis & treatment
Oliguria diagnosis and treatment
Wound healing treatment
Deep Venous Thrombosis prophylaxis treatments
Acid-base disturbance diagnosis and treatment
Electrolyte disturbance diagnosis and treatment Referring again to FIGS. 1 and 2, the remote command center comprises an A/V conferencing server 190. In an embodiment, A/V conferencing server 190 acquires audio and video signals from patient monitoring station "A" and provides a terminal (not shown) access to these signals via external network access 195. In yet another embodiment addition, a local terminal (not shown) operated by a "local visitation participant" or "LVP" and a remote terminal (not shown) operated by a "remote visitation participant" or "RVP" are bridged by A/V conferencing server 190 to provide audio and video signals from the patient monitoring station, the local terminal and the remote terminal available simultaneously to LVP and RVP. Additionally, a terminal user may control the position of camera 205. By way of illustration and not as a limitation, RVPs and LVPs may be patients, nurses, doctors, and other specialists.

The audio and video data may be used to obtain audio and video information about an outpatient. The video data may allow the remote command center to observe the outpatient's appearance, mobility, functional capabilities and alertness. Additionally, video imagery may be used to monitor the condition of wounds, skin rashes and burns for signs of healing, infection and spreading. In conjunction with diagnostic software, the remote command center may also be able to diagnose a skin condition and to order treatment.

The audio and video conferencing capabilities allow for consultations among geographically dispersed healthcare providers.

In an embodiment, when each command center person logs onto the system, a background service is started. This service subscribes to an emergency alert server Emergency messages are passed from the OPCL through the emergency alert server to the command center. As the emergency alert server receives a message the OPCL, it sends a message to all of the subscribed services in the command center. This notification alerts the command center users by means of a "pop-up" alert window at the users' workstation that an emergency condition exists at the OPCL calling for the alert, and that the patient or a local caregiver has requested immediate backup.

To facilitate the emergency call capability, in addition to the various network connections of a more automated type, an emergency "call button" is provided at each OPCL. This could by or near each bed, at a mobile care bed or any location where the patient may be located. When pressed, the call button causes a message to be sent to the emergency alert server at the command center that the outpatient is experiencing an event that requires review by the remote command center. Based on the data available to the remote command center, the remote command center may take appropriate action on behalf of the outpatient. The emergency alert web service identifies the OPCL from the IP address (unique to each video server) and input number it was passed. It then sends a message to all subscribing clients identifying the emergency condition, the patient and the OPCL.

In another embodiment, an OPCL comprises monitoring instruments linked to a wireless network. This serves the needs of those patients who are transported from one location to another (either internal to a hospital or to other hospitals or diagnostic centers) for testing, procedures or other reasons. In this embodiment, monitoring continues using typical monitoring means that have been described above which include, without limitation, physiological monitoring equipment, video monitoring equipment and an emergency call button, all of which transmit their signals in a wireless fashion so that movement of the patient bed does not interrupt the transmission of information.

Figure 7:
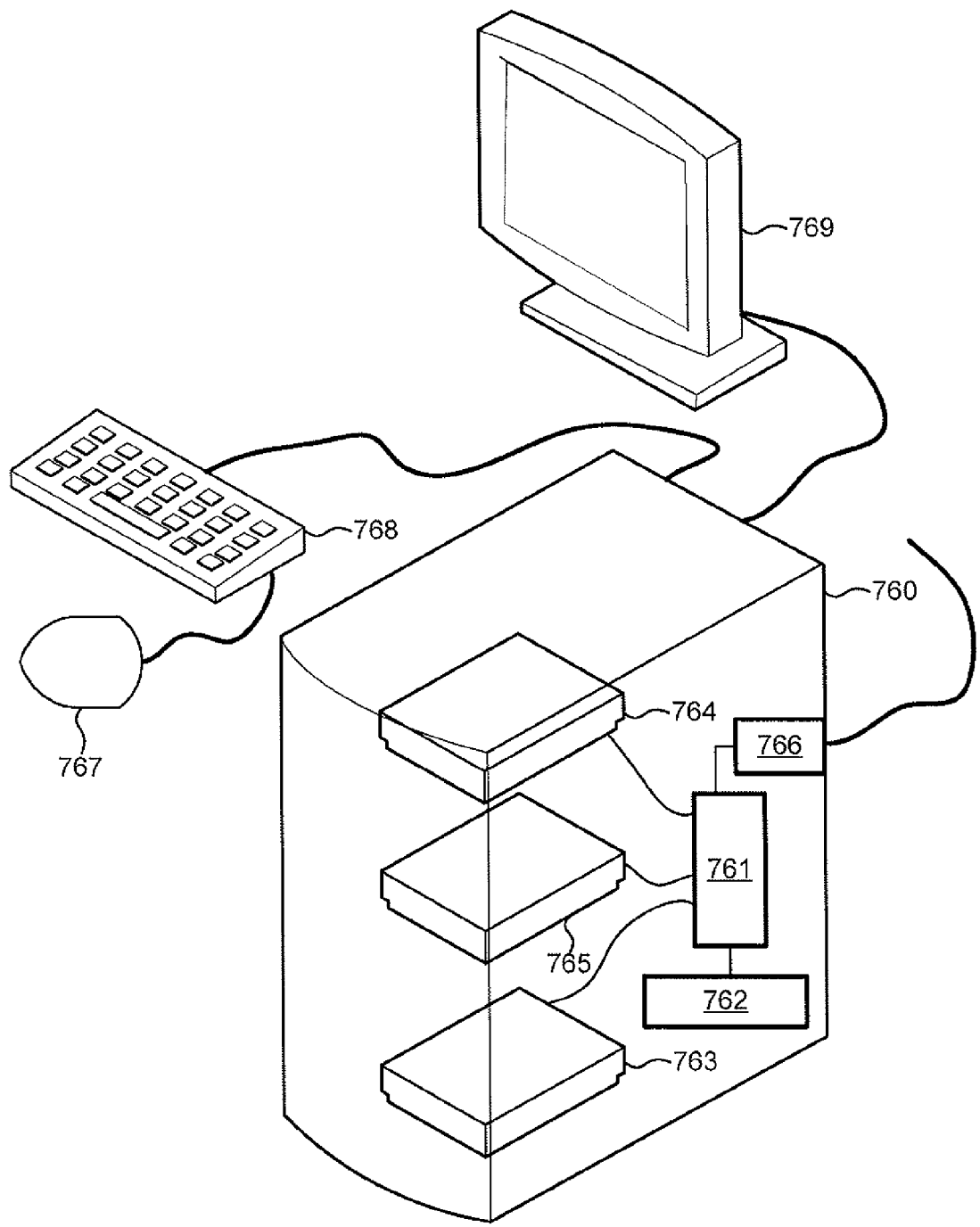
FIG. 7 is a block diagram illustrating functional components of a personal computer.

As previously described, the OPCL and the remote command center may interact using a variety of the computing devices, including a personal computer. By way of illustration, the functionality of the general purpose computer 110 may be implemented on a personal computer 760 illustrated in FIG. 7. Such a personal computer 760 typically includes a processor 761 coupled to volatile memory 762 and a large capacity nonvolatile memory, such as a disk drive 763. The computer 760 may also include a floppy disc drive 764 and a compact disc (CD) drive 765 coupled to the processor 761. Typically the computer device 760 will also include a pointing device such as a mouse 767, a user input device such as a keyboard 768 and a display 769. The computer device 760 may also include a number of connector ports coupled to the processor 761 for establishing data connections or receiving external memory devices, such as a USB or FireWire® connector sockets or other network connection circuits 766 for coupling the processor 761 to a network. In a notebook configuration, the computer housing includes the pointing device 767, keyboard 768 and the display 769 as is well known in the computer arts.

While the capability of the patient monitoring system 105 has been disclosed with respect to a general purpose computer 110 (see, FIG. 1), those skilled in the art will also appreciate that the system can be embodied in a manner that is useful to mobile devices. For example, cell phones, PDA's and other mobile devices may perform some or all of the functions of general purpose computer 110.

Figure 8:
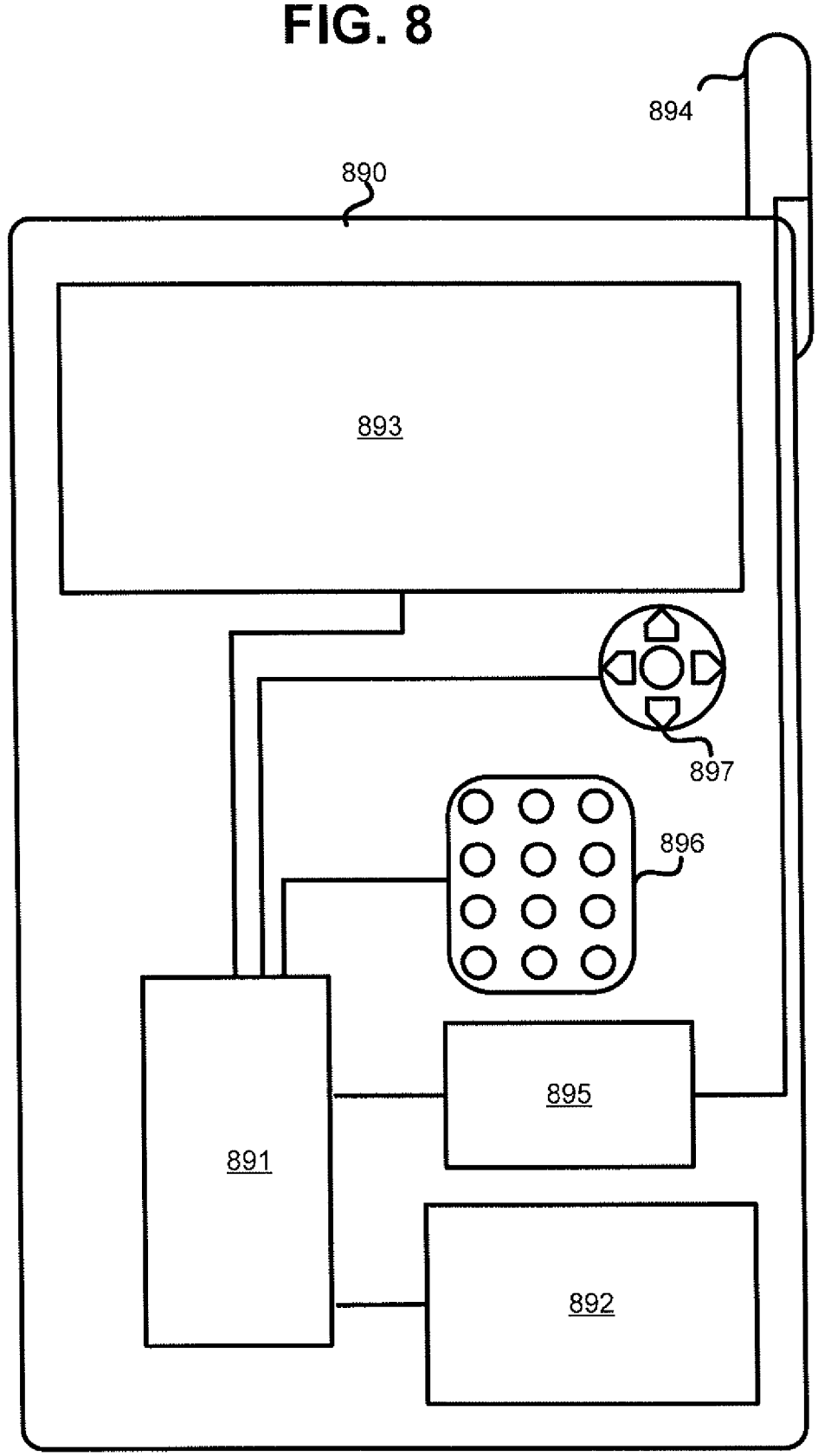
FIG. 8 is a block diagram illustrating functional components of a wireless device.

Typical mobile devices suitable for use with the various embodiments will have in common the components illustrated in FIG. 8. For example, the exemplary mobile device 890 may include a processor 891 coupled to internal memory 892, a display 893 and to a SIM 899 or similar removable memory unit. Additionally, the mobile device 890 may have an antenna 894 for sending and receiving electromagnetic radiation that is connected to a wireless data link and/or cellular telephone transceiver 895 coupled to the processor 891. In some implementations, the transceiver 895 and portions of the processor 891 and memory 892 used for cellular telephone communications are collectively referred to as the air interface since it provides a data interface via a wireless data link. Mobile devices typically also include a key pad 896 or miniature keyboard and menu selection buttons or rocker switches 897 for receiving user inputs.

The processor 891 may be any programmable microprocessor, microcomputer or multiple processor chip or chips that can be configured by software instructions (applications) to perform a variety of functions, including the functions of the various embodiments described herein. In some mobile devices, multiple processors 891 may be provided, such as one processor dedicated to wireless communication functions and one processor dedicated to running other applications. Typically, software applications may be stored in the internal memory 892 before they are accessed and loaded into the processor 891. In some mobile devices, the processor 891 may include internal memory sufficient to store the application software instructions. The internal memory of the processor may include a secure memory 898 which is not directly accessible by users or applications and that is capable of recording MDINs and SIM IDs as described in the various embodiments. As part of the processor, such a secure memory 898 may not be replaced or accessed without damaging or replacing the processor. In some mobile devices, additional memory chips (e.g., a Secure Data (SD) card) may be plugged into the device 890 and coupled to the processor 891. In many mobile devices, the internal memory 892 may be a volatile or nonvolatile memory, such as flash memory, or a mixture of both. For the purposes of this description, a general reference to memory refers to all memory accessible by the processor 891, including internal memory 892, removable memory plugged into the mobile device, and memory within the processor 891 itself, including the secure memory 898.

Figure 9:
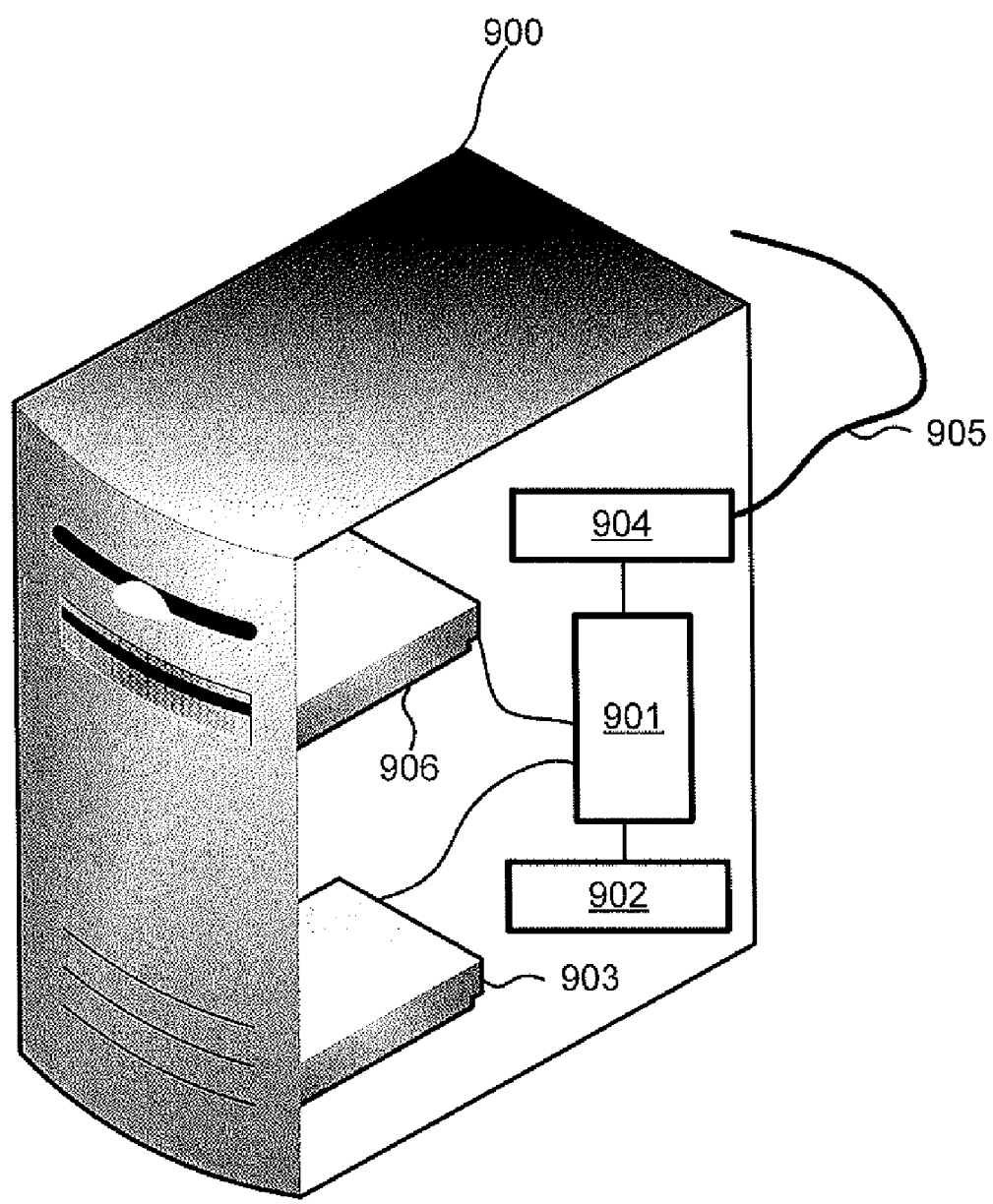
FIG. 9 is a block diagram illustrating functional components of a server.

A number of the aspects described above may also be implemented with any of a variety of remote server devices, such as the server 900 illustrated in FIG. 9. Such a server 900 typically includes a processor 901 coupled to volatile memory 902 and a large capacity nonvolatile memory, such as a disk drive 903. The server 900 may also include a floppy disk drive and/or a compact disc (CD) drive 906 coupled to the processor 901. The server 900 may also include a number of connector ports 904 coupled to the processor 901 for establishing data connections with network circuits 905.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Further, words such as "thereafter," "then," "next," etc. are not intended to limit the order of the steps; these words are simply used to guide the reader through the description of the methods.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of the computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module which may reside on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disc storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a machine readable medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the embodiments shown herein but is to be accorded the widest scope consistent with the principles and novel features disclosed herein. Further, any reference to claim elements in the singular, for example, using the articles "a," "an," or "the," is not to be construed as limiting the element to the singular.

What is claimed is:

1. A system for providing expert care from a remote location to outpatients located at outpatient care locations (OPCLs) comprising:
   a network;
   patient monitoring stations located at the OPCLs for monitoring patient data elements from outpatients, wherein the monitored patient data elements comprise data elements indicative of medical conditions of the outpatients and wherein each patient monitoring station comprises a communications interface that transmits the monitored patient data elements to a remote command center via the network; and
   the remote command center connected to the network, wherein the remote command center comprises a rules engine, wherein the rules engine comprises rules comprising conditions, and wherein the remote command center comprises instructions which when executed by the remote command center cause the remote command center to:
      receive the monitored patient data elements from the OPCLs;
      acquire other patient data elements, wherein the other patient data elements are indicative of the medical conditions of the outpatients and wherein the monitored patient data elements and the other patient data elements are collectively referred to as "patient data elements;"
      utilize the rules engine to apply rules in accordance with the requirements of the rules to at least two patient data elements;
      determine when the conditions of any one of the rules have been satisfied; and
      when the conditions of any one of the rules has been satisfied, taking an action in accordance with the any one of the rules with respect to a particular one of the outpatients to whom the any one of the rules applies, and
   wherein the monitoring and determining when the conditions of the any one of rules has been satisfied occurs in an automated fashion at the remote command whenever the computerized patient care management system determines that the action should be taken.

2. The system of claim 1, wherein the action is selected from the group consisting of issuing an alert with respect to the outpatient, issuing an intervention order with respect to the outpatient, issuing a release protocol and order with respect to the outpatient, and maintaining monitoring of the outpatient.

3. The system of claim 1, wherein a patient monitoring station further comprises monitoring equipment for acquiring patient data elements from an outpatient;
   a storage device for receiving and storing the patient data elements from the monitoring equipment; and
   a communications scheduler for establishing communications between the storage device and the communications interface and for sending the stored patient data elements to the remote command center.

4. The system of claim 3, wherein the communications scheduler establishes communications according to a schedule received from the remote command center.

5. The system of 3, wherein the communications scheduler establishes communications in response to a command received from the remote command center.

6. The system of 3, wherein the patient monitoring station further comprises an urgent consultation warning system and wherein the urgent consultation warning system comprises instructions which when executed by the urgent consultation warning system cause the urgent consultation warning system to:
   evaluate the patient data elements before receipt of the patient data elements at the storage device and to determine if an event has occurred that warrants an urgent consultation; and
   when an urgent consultation is warranted, then instruct the communications scheduler to establish communications between the storage device and the communications interface to send the stored patient data elements to the remote command center.

7. The system of claim 1, wherein one of the at least two patient data elements comprises a physiological data element of the outpatient and another of the at least two patient data elements comprises a clinical data element of the outpatient.

8. The system of claim 1, wherein one of the at least two patient data elements comprises a physiological data element of the outpatient and another of the at least two patient data elements comprises a medication data element of the outpatient.

9. The system of claim 1, wherein one of the at least two patient data elements comprises a physiological data element of the outpatient and another of the at least two patient data elements comprises a laboratory data element of the outpatient.

10. The system of claim 1, wherein one of the at least two patient data elements comprises a clinical data element of the outpatient and another of the at least two patient data elements comprises a laboratory data element of the outpatient.

11. The system of claim 1, wherein one of the at least two patient data elements comprises a physiological data element of the outpatient and another of the at least two patient data elements comprises a physiological data element of the outpatient.

12. The system of claim 1, wherein a monitoring station further comprises monitoring equipment and wherein the monitoring equipment comprises instructions which when executed by the monitoring equipment cause the monitoring equipment to monitor patient data elements from the outpatient and to send the monitored patient data elements to the remote command center via the network.

13. The system of claim 1 further comprising a data server/data warehouse for storing and analyzing data from the remote command center.

14. The system of claim 1 further comprising a decision support system and wherein the decision support system comprises instructions which when executed by the decision support system cause the decision support system to:
receive information relating to a medical condition of an outpatient;
apply a decision support algorithm; and
provide a response based upon application of the decision support algorithm to the information.

15. The system of claim 10 wherein the decision support algorithm comprises a guideline of practice relating to:
Bradyarrhythmias diagnosis & treatment, Congestive heart failure diagnosis & treatment, Fluid resuscitation indications & treatment, Myocardial infarction diagnosis & treatment, MI with left bundle branch block diagnosis, Pulmonary embolism diagnosis, Supra-ventricular tachyarrhythmias diagnosis & treatments, Unstable angina diagnosis & treatment, Venous thromboembolism prophylaxis treatment, Venous thrombosis: diagnosis & treatment, Ventricular arrhythmias diagnosis & treatment, Warfarin treatment, Pneumonia, community acquired diagnosis and treatment, Asthma diagnosis & treatment, Chronic Obstructive Pulmonary Disease diagnosis and treatment, Diuretic treatment, Hyperkalemia: diagnosis & treatment, Hypernatremia: diagnosis & treatment, Hypokalemia: diagnosis & treatment, Hyponatremia: diagnosis & treatment, Oliguria diagnosis and treatment, Wound healing treatment, Deep Venous Thrombosis prophylaxis treatments, Acid-base disturbance diagnosis and treatment, and Electrolyte disturbance diagnosis and treatment.

16. The system of claim 10, wherein the response is selected from the group consisting of a diagnosis, a method of treatment, and a laboratory protocol.

17. The system of claim 1 further comprising an order writing module, and wherein the order writing module comprises instructions which when executed by the order writing module cause the monitoring equipment to provide knowledge-based orders based upon the patient data elements, wherein a knowledge-based order is selected from the group consisting of an authorization to administer medication, an authorization to subject the outpatient to a laboratory protocol, and an authorization to subject the outpatient to a surgical procedure.

18. The system of claim 1 wherein the OPCLs further comprise means for transmitting video and wherein the remote command center further comprises instructions which when executed by the remote command center cause the remote command center to receive and display video.

19. The system of claim 1, wherein the OPCLs further comprise means for transmitting audio and wherein the remote command center comprises instructions which when executed by the remote command center cause the remote command center to receive and reproduce audio.

20. The system of claim 1, wherein the network is selected from the group consisting of a wired network, a wireless network, a satellite network, a public switched telephone network, an IP network, a packet switched network, a cell phone network, a cable network, and a coax network, a hybrid fiber coax network.

21. The system of claim 1, wherein the an OPCL comprises a site assessment module, wherein the site assessment module comprises instructions which when executed by the site assessment module cause the site assessment module to:
receive site assessment data, wherein the site assessment data are indicative of the capability of the OPCL to provide diagnostic and treatment services to the outpatients; and
determine from the site assessment data service level measures of the OPCL indicative of a capability of the OPCL to provide diagnostic and treatment services to the outpatients, and
wherein the communications interface comprises instructions which when executed by the communications interface cause the communication interface to transmit the service level measures to the remote command center by the network, and wherein the remote command center wherein the remote command center further comprises instructions which when executed by the remote command center cause the remote command center to receive the service level measures from the OPCL and create the rules for the outpatients consistent with the service level measures.

22. The system of claim 21 further comprising a decision support system comprising instructions which when executed by the decision support system cause the decision support system to:
receive information relating to the medical conditions of the outpatients;
apply a decision support algorithm to selected data elements consistent with the service level measures; and
provide responses based upon application of the decision support algorithm to the information consistent with the service level measures.

23. The system of claim 22 wherein the decision support algorithm comprises a guideline of practice relating to:
Bradyarrhythmias diagnosis & treatment, Congestive heart failure diagnosis & treatment, Fluid resuscitation indications & treatment, Myocardial infarction diagnosis & treatment, MI with left bundle branch block diagnosis, Pulmonary embolism diagnosis, Supra-ventricular tachyarrhythmias diagnosis & treatments, Unstable angina diagnosis & treatment, Venous thromboembolism prophylaxis treatment, Venous thrombosis: diagnosis & treatment, Ventricular arrhythmias diagnosis & treatment, Warfarin treatment, Pneumonia, community acquired diagnosis and treatment, Asthma diagnosis & treatment, Chronic Obstructive Pulmonary Disease diagnosis and treatment, Diuretic treatment, Hyperkalemia: diagnosis & treatment, Hypernatremia: diagnosis & treatment, Hypokalemia: diagnosis & treatment, Hyponatremia: diagnosis & treatment, Oliguria diagnosis and treatment, Wound healing treatment, Deep Venous Thrombosis prophylaxis treatments, Acid-base disturbance diagnosis and treatment, and Electrolyte disturbance diagnosis and treatment.

24. The system of claim 22, wherein the response is selected from the group consisting of a diagnosis, a method of treatment, and a laboratory protocol.

25. The system of claim 22, wherein the decision support system further comprises instructions which when executed by the decision support system cause the decision support system to:
 access an order writing module; and
 issue an order consistent with the service level measures, wherein the order is selected from the group consisting of an authorization to administer medication, an authorization to subject the outpatient to a laboratory protocol, and an authorization to subject the outpatient to a surgical procedure.

26. The system of claim 21, wherein the site assessment module further comprises instructions which when executed by the site assessment module cause the site assessment module to:
 prompt a user for the site assessment data; and
 determine the service level measures based on the user response.

27. The system of claim 21, wherein the patient monitoring station comprises a site assessment code and the site assessment module further comprises instructions which when executed by the site assessment module cause the site assessment module to:
 acquire the site assessment code from the patient monitoring station; and
 determine the service level measures at least in part based on the site assessment code.

28. The system of claim 21, wherein the service level measures comprise:
 an inventory of available monitoring data elements;
 an inventory of available diagnostic services;
 an inventory of available surgical treatment services; and
 an inventory of available laboratory services.

29. A method for providing expert critical care from a remote location to outpatients located at outpatient care locations (OPCLs) comprising:
 communicating over a network monitored patient data elements from monitoring stations, wherein the monitoring stations comprise instructions for obtaining the monitored patient data elements of the outpatients to a remote command center, wherein the remote command center comprises a computerized patient care management system, which system utilizes a rules engine to apply rules, repeatedly and automatically to at least two patient data elements, wherein the rules applied by the rules engine identify existing or potential patient conditions that may warrant management by a health care provider;
 acquiring at the remote command center other patient data elements, wherein the other patient data elements are indicative of the medical conditions of the outpatients and wherein the monitored patient data elements and the other patient data elements are collectively referred to as "patient data elements;" and
 using the rules engine to apply the rules to at least two patient data elements;
 determining when the conditions of any one of the rules have been satisfied; and
 when the conditions of any one of the rules has been satisfied, taking an action in accordance with the rule with respect to a particular one of the outpatients to whom the any one of the rules applies, and
 wherein the monitoring and determining when the conditions of the any one of rules has been satisfied occurs in an automated fashion at the remote command the computerized patient care management system determines that an alert should be displayed.

30. The method of claim 29, wherein the action is selected from the group consisting of issuing an alert with respect to the outpatient, issuing an intervention order with respect to the outpatient, issuing a release protocol and order with respect to the outpatient, and maintaining monitoring of the outpatient.

31. The method of claim 29 further comprising:
 receiving and storing the patient data elements from patient monitoring equipment in a storage device; and
 establishing communications between the storage device and the communications interface using a communications scheduler; and
 sending the stored patient data elements to the remote command center over the network.

32. The method of claim 31, wherein establishing communications between the storage device and the communications interface using a communications scheduler comprises the computerized patient care management system establishing communications between the storage device and the communications interface using a communications scheduler according to a schedule received from the remote command center.

33. The method of 31, wherein establishing communications between the storage device and the communications interface using a communications scheduler comprises the computerized patient care management system establishing communications between the storage device and the communications interface using a communications scheduler according to a command received from the remote command center.

34. The method of 31, wherein the patient monitoring station further comprises a computerized urgent consultation warning system and wherein the method further comprises:
 evaluating by the urgent consultation warning system the patient data elements using the urgent consultation warning system before receipt of the patient data elements at the storage device;
 determining by the urgent consultation warning system whether an event has occurred that warrants an urgent consultation; and
 when an urgent consultation is warranted, then the urgent consultation warning system instructing the communications scheduler to establish communications between the storage device and the communications interface to send the stored patient data elements to the remote command center.

35. The method of claim 29, wherein the at least two patient data elements comprise a physiological measure and a clinical data element of the outpatient.

36. The method of claim 29, wherein the at least two patient data elements comprise a physiological data element of the outpatient and a medication data element of the outpatient.

37. The method of claim 29, wherein the at least two patient data elements comprise a physiological data element of the outpatient and a laboratory data element of the outpatient.

38. The method of claim 29, wherein the at least two patient data elements comprise a clinical data element of the outpatient and a laboratory data element of the outpatient.

39. The method of claim 29, wherein the at least two patient data elements comprise two physiological data elements of the outpatient.

40. The method of claim 29 further comprising:
 receiving information relating to a medical condition of an outpatient from the monitoring stations;

applying a decision support algorithm by the computerized patient care management system to selected data elements of the outpatient; and providing a response from the computerized patient care management system based upon application of the decision support algorithm to the information.

41. The method of claim 40 wherein the decision support algorithm comprises a guideline of practice relating to:

Bradyarrhythmias diagnosis & treatment, Congestive heart failure diagnosis & treatment, Fluid resuscitation indications & treatment, Myocardial infarction diagnosis & treatment, MI with left bundle branch block diagnosis, Pulmonary embolism diagnosis, Supra-ventricular tachyarrhythmias diagnosis & treatments, Unstable angina diagnosis & treatment, Venous thromboembolism prophylaxis treatment, Venous thrombosis: diagnosis & treatment, Ventricular arrhythmias diagnosis & treatment, Warfarin treatment, Pneumonia, community acquired diagnosis and treatment, Asthma diagnosis & treatment, Chronic Obstructive Pulmonary Disease diagnosis and treatment, Diuretic treatment, Hyperkalemia: diagnosis & treatment, Hypernatremia: diagnosis & treatment, Hypokalemia: diagnosis & treatment, Hyponatremia: diagnosis & treatment, Oliguria diagnosis and treatment, Wound healing treatment, Deep Venous Thrombosis prophylaxis treatments, Acid-base disturbance diagnosis and treatment, and Electrolyte disturbance diagnosis and treatment.

42. The method of claim 40, wherein the response is selected from the group consisting of a diagnosis, a method of treatment, and a laboratory protocol.

43. The method of claim 29 further comprising:
accessing an order writing module; and
issuing an order by the computerized patient care management system, wherein the order is selected from the group consisting of an authorization to administer medication, an authorization to subject the outpatient to a laboratory protocol, and an authorization to subject the outpatient to a surgical procedure.

44. The method of claim 29 further comprising transmitting video from an OPCL via the network to the remote command center.

45. The method of claim 29 further comprising transmitting audio from an OPCL via the network to the remote command center.

46. The method of claim 29, wherein the network is selected from the group consisting of a wired network, a wireless network, a satellite network, a public switched telephone network, an IP network, a packet switched network, a cell phone network, a cable network, and a coax network, a hybrid fiber coax network.

47. The method of claim 29 further comprising:
receiving site assessment data over the network, wherein the site assessment data are indicative of the capability of an OPCL to provide diagnostic and treatment services to patients;
determining by the computerized patient care management system service level measures of the OPCL indicative of a capability of the OPCL to provide diagnostic and treatment services to patients; and
communicating by computerized patient care management system over the network the service level measures to a remote command center, and wherein creating the rules for the outpatient further comprises creating the rules consistent with the service level measures.

48. The method of claim 47, wherein the method further comprises:
receiving information from the monitoring stations relating to the medical conditions of the outpatients;
applying a decision support algorithm by the computerized patient care management system to selected data elements of the outpatients consistent with the service level measures; and
providing responses based upon application of the decision support algorithm by the computerized patient care management system to the information consistent with the service level measures.

49. The method of claim 48 wherein the decision support algorithm comprises a guideline of practice relating to:

Bradyarrhythmias diagnosis & treatment, Congestive heart failure diagnosis & treatment, Fluid resuscitation indications & treatment, Myocardial infarction diagnosis & treatment, MI with left bundle branch block diagnosis, Pulmonary embolism diagnosis, Supra-ventricular tachyarrhythmias diagnosis & treatments, Unstable angina diagnosis & treatment, Venous thromboembolism prophylaxis treatment, Venous thrombosis: diagnosis & treatment, Ventricular arrhythmias diagnosis & treatment, Warfarin treatment, Pneumonia, community acquired diagnosis and treatment, Asthma diagnosis & treatment, Chronic Obstructive Pulmonary Disease diagnosis and treatment, Diuretic treatment, Hyperkalemia: diagnosis & treatment, Hypernatremia: diagnosis & treatment, Hypokalemia: diagnosis & treatment, Hyponatremia: diagnosis & treatment, Oliguria diagnosis and treatment, Wound healing treatment, Deep Venous Thrombosis prophylaxis treatments, Acid-base disturbance diagnosis and treatment, and Electrolyte disturbance diagnosis and treatment.

50. The method of claim 48, wherein the response is selected from the group consisting of a diagnosis, a method of treatment, and a laboratory protocol.

51. The method of claim 48 further comprising:
accessing by the computerized patient care management system an order writing module; and
issuing by the computerized patient care management system an order consistent with the service level measures.

52. The method of claim 51, wherein the order is selected from the group consisting of an authorization to administer medication, an authorization to subject the outpatient to a laboratory protocol, and an authorization to subject the outpatient to a surgical procedure.

53. The method of claim 47, wherein the method further comprises:
prompting by the computerized patient care management system a user for the site assessment information; and
determining by the computerized patient care management system the service level measures based on the user response.

54. The method of claim 47, wherein the patient monitoring station comprises a site assessment code and the method further comprises:
acquiring by the computerized patient care management system the site assessment code from the patient monitoring station; and
determining by the computerized patient care management system the service level measures at least in part based on the site assessment code.

55. The method of claim 47, wherein the service level measures comprise
an inventory of available monitoring data elements.

56. A system for providing expert care from a remote location to outpatients located at outpatient care locations (OPCLs) comprising:
  a network;
  patient monitoring stations located at the OPCLs for monitoring patient data elements from outpatients, wherein the monitored patient data elements comprise data elements indicative of a heart condition of the outpatients and wherein each patient monitoring station comprises a communications interface that transmits the monitored patient data elements to a remote command center via the network; and
  the remote command center connected to the network, wherein the remote command center comprises a rules engine, wherein the rules engine comprises rules comprising conditions, and wherein the remote command center comprises instructions which when executed by the remote command center cause the remote command center to:
    receive the monitored patient data elements from the OPCLs;
    acquire other patient data elements, wherein the other patient data elements are indicative of the heart condition of the outpatients and wherein the monitored patient data elements and the other patient data elements are collectively referred to as "patient data elements;"
    utilize the rules engine to apply rules in accordance with the requirements of the to at least two patient data elements;
    determine when the conditions of any one of the rules have been satisfied; and
    when the conditions of the any one of the rule has been satisfied, taking an action in accordance with the any one of the rules with respect to a particular one of the outpatients to whom the any one of the rules applies, and
  wherein the monitoring and determining when the conditions of the any one of rules has been satisfied occurs in an automated fashion at the remote command center by the computerized patient care management system determines that the action should be taken.

* * * * *